United States Patent
Marro et al.

(10) Patent No.: US 11,912,854 B2
(45) Date of Patent: Feb. 27, 2024

(54) PTFE LINERS WITH REDUCED COEFFICIENT OF FRICTION

(71) Applicant: Zeus Industrial Products, Inc., Orangeburg, SC (US)

(72) Inventors: Justin A. Marro, Orangeburg, SC (US); John Richard Campanelli, West Columbia, SC (US); Patrick Cooper, Orangeburg, SC (US); Robert L. Ballard, Lexington, SC (US); Douglas Lee Tourville, Orangeburg, SC (US)

(73) Assignee: ZEUS COMPANY INC., Orangeburg, SC (US)

( * ) Notice: Subject to any disclaimer, the term of this patent is extended or adjusted under 35 U.S.C. 154(b) by 0 days.

(21) Appl. No.: 17/330,956

(22) Filed: May 26, 2021

(65) Prior Publication Data
US 2021/0371638 A1    Dec. 2, 2021

Related U.S. Application Data

(60) Provisional application No. 63/030,640, filed on May 27, 2020, provisional application No. 63/030,367, filed on May 27, 2020.

(51) Int. Cl.
C08L 27/18 (2006.01)
A61M 39/08 (2006.01)

(52) U.S. Cl.
CPC ............. *C08L 27/18* (2013.01); *A61M 39/08* (2013.01); *A61M 2205/0222* (2013.01); *C08L 2203/02* (2013.01); *C08L 2205/025* (2013.01)

(58) Field of Classification Search
CPC ........... A61B 17/3431; Y10T 428/1397; A61L 29/085; A61M 25/0021; A61M 25/0023; A61M 25/0222; A61M 39/08; B32B 1/08; C08L 27/18
USPC ............... 428/36.9, 36.91, 36.92; 604/508, 604/523–539, 915–921
See application file for complete search history.

(56) References Cited

U.S. PATENT DOCUMENTS

| | | | |
|---|---|---|---|
| 3,652,409 A * | 3/1972 | Mack | C08L 79/08 508/106 |
| 6,863,852 B1 | 3/2005 | Ballard et al. | |
| 10,744,231 B1 | 8/2020 | Wahab et al. | |
| 2002/0156459 A1* | 10/2002 | Ye | A61M 25/0053 604/527 |

(Continued)

FOREIGN PATENT DOCUMENTS

CN    110292663 A    10/2019

OTHER PUBLICATIONS

Burris, D.L. et al., A low friction and ultra low wear rate PEEK/PTFE composite, Wear, 261, 2006 (Year: 2006).*

(Continued)

*Primary Examiner* — Lee E Sanderson
(74) *Attorney, Agent, or Firm* — Jessica L. Gorczynski; Womble Bond Dickinson (US) LLP

(57) ABSTRACT

The present disclosure provides extruded PTFE composite tubes with a reduced coefficient of friction (COF). In some embodiments, such extruded PTFE composite tubes may exhibit a reduced change in coefficient of friction between about 20° C. and about 40° C. with the inclusion of secondary polymeric particles with small particle sizes (<100 μm) at loading percentages of less than about 50 weight %.

23 Claims, 4 Drawing Sheets

(56) References Cited

U.S. PATENT DOCUMENTS

| | | | |
|---|---|---|---|
| 2006/0029795 A1 | 2/2006 | Sawyer et al. | |
| 2006/0030681 A1* | 2/2006 | Sawyer | C08L 71/00 525/471 |
| 2012/0061119 A1* | 3/2012 | Schlipf | C08L 71/00 524/508 |
| 2013/0289531 A1 | 10/2013 | Pagan et al. | |
| 2015/0025562 A1* | 1/2015 | Dinh | A61M 25/0045 264/238 |
| 2015/0203679 A1* | 7/2015 | Ueda | C08L 71/00 525/151 |
| 2016/0237189 A1 | 8/2016 | Taira et al. | |

OTHER PUBLICATIONS

Onodera et al., Structure and Function of Transfer Film Formed from PTFE/PEEK Polymer Blend, The Journal of Physical Chemistry, 2017, 121 (Year: 2017).*

International Search Report and Written Opinion for PCT/US2021/034213, filed May 26, 2021—dated Sep. 23, 2021.

\* cited by examiner

PTFE LINERS WITH REDUCED COEFFICIENT OF FRICTION

CROSS-REFERENCE TO RELATED APPLICATION

The present application claims priority to U.S. Provisional Patent Application No. 63/030,367, filed May 27, 2020 and U.S. Provisional Patent Application No. 63/030,640, filed May 27, 2020, which are incorporated by reference in their entireties.

FIELD OF THE INVENTION

The present application relates generally to the field of poly(tetrafluoroethylene) (PTFE) liners and products comprising such PTFE liners.

BACKGROUND

Poly(tetrafluoroethylene) (PTFE) resin is used in paste extrusion processes to manufacture such products as sheets, profiles, monofilaments, and tubes. Paste extrusion of PTFE generally involves several steps, including: (1) paste preparation or resin mixing with lubricants; (2) preforming; (3) paste extrusion through one or more die heads; and (4) devolatilization. PTFE is commonly used for inner liners of catheters due, e.g., to its chemical resistance, biocompatibility and low coefficient of friction (COF). PTFE exhibits unique characteristics in this field that other polymers do not. Due to the low COF associated with PTFE materials, use of PTFE materials can provide tubes with an inner diameter that easily allows various catheter technologies such as stents, balloons, atherectomy or thrombectomy devices to be pushed through a small diameter catheter lumen. The effect of increased lubricity of the catheter inner diameter (ID) is a reduced deployment force of catheter devices as the catheter devices are passed through the lumen, increasing the likelihood of a successful procedure employing such devices. During typical medical procedures, the difference between operating suite temperatures (ranging between 65° F. and 75° F. or 18-24° C.) and body temperature (98.6° F. or 37° C.) can substantially change the properties of the medical component materials—especially PTFE components such as catheter liners. With PTFE having notable thermal transitions at approximately 19° C. and 30° C., the modulus is highly varied around the operating room temperatures and the overall COF of PTFE-based materials used can be dependent on the modulus of the material. These thermal transitions affect physical properties in such a way as to be detrimental to the performance of PTFE liners in catheters during minimally invasive medical procedures in which the liners are exposed to temperatures varying from under 20° C. to around 40° C.

It is desirable to provide ways to reduce the COF of extruded polymer films, profiles and tubes composed of PTFE in order to improve the lubricity of such extruded polymer films, profiles and tubes for use in various catheter technologies. Adding certain fillers such as glass, polyarylene and polyimide polymeric particles to PTFE materials using paste extrusion processes in order to improve wear and creep resistance of such composite PTFE materials have previously been studied in the art. Various methods known in the art involve thermoplastic processing, paste extrusion, and molding of polymeric particles to provide thick-walled (e.g., about 10 mm wall thickness) composite tubes having improved wear and/or creep resistance. However, current methods of adding polymer-based fillers or particles to PTFE sheets, profiles, and tubes have been shown to confer little effect on the COF of the resulting PTFE composite materials and extrudates formed using such methods. It would be advantageous to provide further methods for preparing PTFE-based products using paste extrusion processes, wherein the resulting products exhibit positive COF characteristics.

SUMMARY

The disclosure provides composite PTFE materials (e.g., in the form of sheets, profiles, tubes, etc.) having a reduced coefficient of friction (COF) compared to corresponding PTFE products (which are not composite materials, as described herein). Composite PTFE tubes as provided herein can exhibit significant reduction in the COF relative to a comparable PTFE tube, can exhibit a lower storage modulus as compared to a comparable PTFE tube, and can be in the form of thin-walled tubes, e.g., having a wall thickness of less than about 0.1 mm. The disclosure further provides methods of obtaining such thin-walled composite PTFE tubes having reduced COF and storage modulus as compared to a comparable PTFE tube, as well as methods of using such thin-walled composite PTFE tubes.

In one aspect, the disclosure provides PTFE composite tubes having a reduced coefficient of friction and/or a lower storage modulus as compared to a comparable virgin PTFE tube. In some embodiments, for example, PTFE composite tubes according to the disclosure may comprise PTFE and a second polymer. In such embodiments, the second polymer may be present in a concentration of less than about 50% by weight of the PTFE composite tube. In certain embodiments, the concentration of the second polymer is less than 10% by weight of the PTFE composite tube. PTFE composite tubes according to the disclosure may exhibit one or more beneficial characteristics when compared to a virgin PTFE tube. Such characteristics may include, but are not limited to, a lower coefficient of friction as compared to a comparable PTFE tube when tested at 23° C. and/or a smaller change in coefficient of friction from about 23° C. to about 40° C. as compared to a comparable PTFE tube.

In one or more embodiments, a PTFE composite tube according to the present disclosure can exhibit a coefficient of friction of about 0.07 or less at 23° C. and an increase in coefficient of friction of about 0.02 or less from about 23° C. to about 40° C. In certain embodiments, the PTFE composite tube exhibits a lower storage modulus as compared to a PTFE tube at 20° C. and a reduced change in storage modulus between 20° C. to 40° C. as compared to a PTFE tube. In some embodiments, a PTFE composite tube according to the present disclosure can exhibit a storage modulus of about 15×108 Pa or less at 20° C. and a decrease in storage modulus of about 7.5×108 Pa or less from about 20° C. to about 40° C.

Generally, a PTFE composite tube according to the present disclosure can comprise a second polymer which is different from PTFE. For example, in some embodiments, the second polymer is a polyolefin or modified polyolefin. In some embodiments, the second polymer is a fluoropolymer or a modified fluoropolymer. In some embodiments, the second polymer is a polyarylketone (PAEK), a polyetheretherketone (PEEK), or a modified PAEK or PEEK. In certain embodiments, the second polymer is a polyester or modified polyester, or a polyurethane or modified polyurethane. In some embodiments, the second polymer is a polyimide, polyamide, polyamine, or a copolymer thereof. In some embodiments, the second polymer may be in the form of a plurality of particles or in the form of a powder and those particles may have a certain particle size. In some embodiments, for example, the second polymer can be in the form of a plurality of polymeric particles having an average particle size of less than about 100 microns.

In one or more embodiments, the second polymer in the PTFE composite tube is a second, different PTFE selected from the group consisting of sintered PTFE, reground PTFE, PTFE of a different grade, chemically modified PTFE, and combinations thereof. In still other embodiments, the second polymer may be selected from the group consisting of polyaryletherketone (PAEK), modified polyaryletherketone (modified PAEK), polyetheretherketone (PEEK), modified polyetheretherketone (modified PEEK), polyimide (PI), ultra high molecular weight polyethylene (UHMWPE), fluorinated ethylene propylene (FEP), perfluoroalkoxy alkane (PFA), and combinations or copolymers of any two or more thereof.

In some embodiments, a PTFE composite tube according to the present disclosure has a wall thickness of less than about 0.1 mm. As noted herein, in some embodiments, a PTFE composite tube according to the present disclosure may exhibit certain beneficial properties or characteristics when compared to a comparable PTFE tube. Typically, a comparable PTFE tube as described herein may be an unfilled PTFE tube or a virgin PTFE tube.

Some aspects of the present disclosure provide medical devices comprising a PTFE composite tube as prepared according to one or more embodiments of the present disclosure. For example, the medical device may be a catheter or other catheter technology. In some embodiments, for example, the disclosure provides a medical device comprising a PTFE composite tube. In such embodiments, the PTFE composite tube may comprise PTFE and a second polymer, the second polymer concentration being less than about 50% by weight of the PTFE composite tube. In such embodiments, the PTFE composite tube and/or medical device may exhibit one or both of a lower storage modulus as compared to a PTFE tube at 20° C. and a reduced change in storage modulus between 20° C. to 40° C. as compared to a PTFE tube.

The present disclosure includes, without limitation, the following embodiments.

Embodiment 1

A PTFE composite tube comprising PTFE and a second polymer, wherein the second polymer is present in a concentration of less than about 50% by weight of the PTFE composite tube, and wherein the PTFE composite tube exhibits one or both of: a lower coefficient of friction as compared to a comparable PTFE tube when tested at 23° C.; and a smaller change in coefficient of friction from about 23° C. to about 40° C. as compared to a comparable PTFE tube.

Embodiment 2

The PTFE composite tube of embodiment 1, wherein the concentration of the second polymer is less than 10% by weight of the PTFE composite tube.

Embodiment 3

The PTFE composite tube according to any of embodiments 1-2, wherein the PTFE composite tube exhibits a coefficient of friction of about 0.07 or less at 23° C. and an increase in coefficient of friction of about 0.02 or less from about 23° C. to about 40° C.

Embodiment 4

The PTFE composite tube according to any of embodiments 1-3, wherein the PTFE composite tube exhibits a lower storage modulus as compared to a PTFE tube at 20° C. and a reduced change in storage modulus between 20° C. to 40° C. as compared to a PTFE tube.

Embodiment 5

The PTFE composite tube according to any of embodiments 1-4, wherein the PTFE composite tube exhibits a storage modulus of about $15 \times 10^8$ Pa or less at 20° C. and a decrease in storage modulus of about $7.5 \times 10^8$ Pa or less from about 20° C. to about 40° C.

Embodiment 6

The PTFE composite tube according to any of embodiments 1-5, wherein the second polymer is a polyolefin or modified polyolefin.

Embodiment 7

The PTFE composite tube according to any of embodiments 1-6, wherein the second polymer is a fluoropolymer or a modified fluoropolymer.

Embodiment 8

The PTFE composite tube according to any of embodiments 1-7, wherein the second polymer is a polyarylketone (PAEK), a polyetheretherketone (PEEK), or a modified PAEK or PEEK.

Embodiment 9

The PTFE composite tube according to any of embodiments 1-8, wherein the second polymer is a polyester or modified polyester.

Embodiment 10

The PTFE composite tube according to any of embodiments 1-9, wherein the second polymer is a polyurethane or modified polyurethane.

Embodiment 11

The PTFE composite tube according to any of embodiments 1-10, wherein the second polymer is a polyimide, polyamide, polyamine, or a copolymer thereof.

Embodiment 12

The PTFE composite tube according to any of embodiments 1-11, wherein the second polymer is in the form of a plurality of polymeric particles having an average particle size of less than about 100 microns.

Embodiment 13

The PTFE composite tube according to any of embodiments 1-12, wherein the second polymer is a second, different PTFE selected from the group consisting of sintered PTFE, reground PTFE, PTFE of a different grade, chemically modified PTFE, and combinations thereof.

Embodiment 14

The PTFE composite tube according to any of embodiments 1-13, wherein the second polymer is selected from the group consisting of polyaryletherketone (PAEK), modified polyaryletherketone (modified PAEK), polyetheretherketone (PEEK), modified polyetheretherketone (modified PEEK), polyimide (PI), ultra high molecular weight polyethylene (UHMWPE), fluorinated ethylene propylene (FEP), perfluoroalkoxy alkane (PFA), and combinations or copolymers of any two or more thereof.

Embodiment 15

The PTFE composite tube according to any of embodiments 1-14, wherein the PTFE composite tube has a wall thickness of less than about 0.1 mm.

Embodiment 16

The PTFE composite tube according to any of embodiments 1-15, wherein the comparable PTFE tube is an unfilled PTFE tube.

Embodiment 17

The PTFE composite tube according to any of embodiments 1-16, wherein the comparable PTFE tube is a virgin PTFE tube.

Embodiment 18

A medical device comprising the PTFE composite tube according to any of embodiments 1-17.

Embodiment 19

The medical device of embodiment 18, wherein the medical device is a catheter.

Embodiment 20

A PTFE composite tube comprising PTFE and a second polymer, wherein the second polymer is present in a concentration of less than about 50% by weight of the PTFE composite tube, and wherein the PTFE composite tube exhibits one or both of: a lower storage modulus as compared to a PTFE tube at 20° C.; and a smaller change in storage modulus between 20° C. to 40° C. as compared to a PTFE tube.

Embodiment 21

The PTFE composite tube of embodiment 20, wherein the PTFE composite tube exhibits a storage modulus of about 15×10⁸ Pa or less at 20° C. and a decrease in storage modulus of about 7.5×10⁸ Pa or less from about 20° C. to about 40° C.

Embodiment 22

A medical device comprising a PTFE composite tube, the PTFE composite tube comprising: PTFE and a second polymer, the second polymer concentration being less than about 50% by weight of the PTFE composite tube, the PTFE composite tube exhibiting one or both of: a lower storage modulus as compared to a PTFE tube at 20° C.; and a reduced change in storage modulus between 20° C. to 40° C. as compared to a PTFE tube.

These and other features, aspects, and advantages of the disclosure will be apparent from a reading of the following detailed description together with the accompanying drawings, which are briefly described below. The invention includes any combination of two, three, four, or more of the above-noted embodiments as well as combinations of any two, three, four, or more features or elements set forth in this disclosure, regardless of whether such features or elements are expressly combined in a specific embodiment description herein. This disclosure is intended to be read holistically such that any separable features or elements of the disclosed invention, in any of its various aspects and embodiments, should be viewed as intended to be combinable unless the context clearly dictates otherwise. Other aspects and advantages of the present invention will become apparent from the following.

BRIEF DESCRIPTION OF THE DRAWINGS

In order to provide an understanding of embodiments of the invention, reference is made to the appended drawings, which are not necessarily drawn to scale, and in which reference numerals refer to components of exemplary embodiments of the invention. The drawings are exemplary only, and should not be construed as limiting the invention.

DETAILED DESCRIPTION

The present invention now will be described more fully hereinafter. This invention may, however, be embodied in many different forms and should not be construed as limited to the embodiments set forth herein; rather, these embodiments are provided so that this disclosure will be thorough and complete, and will fully convey the scope of the invention to those skilled in the art. As used in this specification and the claims, the singular forms "a," "an," and "the" include plural referents unless the context clearly dictates otherwise.

The disclosure provides PTFE composite tubes (e.g., including PTFE and one or more additional polymers), e.g., extruded PTFE composite tubes. PTFE composite tubes as provided herein are characterized, at least in part, by a reduced coefficient of friction (COF) as compared with comparable PTFE tubes and a lower storage modulus as compared with comparable PTFE tubes. In some embodiments, PTFE composite tubes as provided herein can be characterized, at least in part, as being "thin-walled" tubes, e.g., having a wall thickness of less than about 0.1 mm. As used herein, a "comparable PTFE tube" refers to a tube having the same size, shape, and wall thickness as a PTFE composite tube described herein, but without the second polymer included therein. For example, a comparable PTFE tube may be characterized as consisting essentially of virgin PTFE without any fillers. Methods for providing PTFE composite tubes, as well as methods of using such PTFE composite tubes and products including such PTFE composite tubes are also provided herein.

Figure 1:
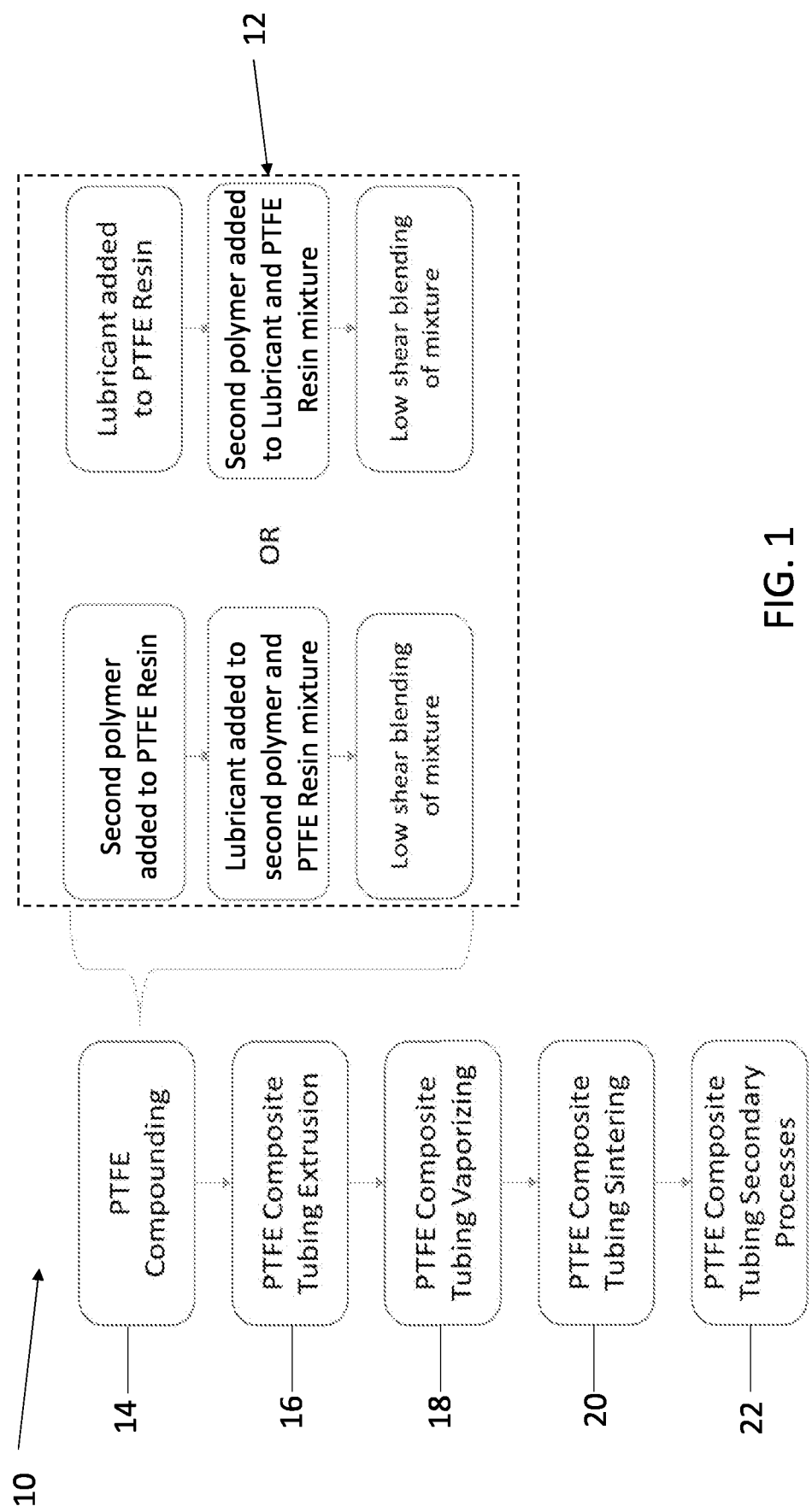
FIG. 1 is a general schematic of a process for producing PTFE composite tubes according to certain embodiments of the present disclosure.

A general schematic of one, non-limiting embodiment of a paste extrusion-based method for producing PTFE composite tubes, e.g., PTFE composite tubes exhibiting the physical properties described herein above, is shown in FIG. 1. As shown in FIG. 1, one method of preparing a PTFE composite tube according to the present disclosure includes preparing a PTFE composite material 12, subjecting the PTFE composite material to compression/compounding step 14 to create a preform, subjecting the preform to an extrusion process 16, e.g., by a paste extrusion machine and sintering the extrudate 20 to form films, tubes or rods, thereby incorporating a second polymer into the product that is extruded (e.g., the film, tube, rod, etc.), creating a PTFE composite extrudate (e.g., a PTFE composite tube). In FIG. 1, method 10 is shown as also including a further step 22 of conducting secondary processes on the PTFE composite extrudate; it is noted that this step is optional, as will be described herein below in further detail.

In one or more embodiments, a method 10 of preparing a PTFE composite tube starts with preparing a PTFE composite material 12 by mixing a PTFE resin, a second polymer, and a lubricant or organic solvent. As used herein, a "PTFE resin" refers to a synthetic fluoropolymer of tetrafluoroethylene which is commonly referred to as polytetrafluoroethylene ("PTFE") or virgin PTFE because it has not been chemically modified. Fine powder PTFE resins that are suitable for paste extrusion processes can be extruded, e.g., at a reduction ratio exceeding 300. Exemplary resins suitable for this purpose include, but are not limited to, Daikin F205, F201, F201L, F208, and F207 resins, Dyneon TF 2071, TF 2072, and TF 2053 resins, Chemours Teflon 640XT X, 641XT X, CFP 6000 X, 62XT X, 6C X, and 6CN X and Asahi Glass CD 090E, and CD 097E. It is to be understood that the products and methods described herein are not limited to such resins, and any PTFE resins can be reasonably used within the scope of the present disclosure. Although the disclosure refers herein, e.g., to "PTFE" resins and "PTFE tubes," it is noted that these materials may not comprise 100% PTFE, but are nonetheless encompassed by the present disclosure. For example, PTFE resins commonly used in paste extrusion can be homopolymeric or non-homopolymeric (e.g., as modified resins with a small amount of comonomer are commonly employed due to lower transition temperature), and all such resins are intended to be encompassed within the scope of the disclosure.

Examples of suitable lubricants and organic solvents include, but are not limited to, Isopar (C, E, G, H, J, K, L, M, N, P, V), Novec (7100, 7200, 7300, 7500, 7700), Naphtha, Shell Sol 340 HT, Shell Sol 142 HT, Mineral spirit 200 HT, methyl nonafluorobutylether, methylnonafluoro-2-butylether, ethyl nonafluorobutylether, ethylnonafluoro-2-butylether, pentane,1,1,1,2,2,3,4,5,5,5-decafluoro-3-methoxy-4-(trifluoromethyl)-, 2-trifluoromethyl-3-ethoxydodecofluorohexane, furan,2,3,3,4,4-pentafluorotetrahydro-5-methoxy-2,5-bis[1,2,2,2-tetrafluoro-1-(trifluoromethyl)ethyl]-, perfluorooctane, perfluoro(2-butyltetrahydrofuran), perfluorotributylamine, 1,1,2,2,3,3,4,4,4-nonafluoro-N,N-bis(nonafluorobutyl)butan-1-amine, C5-18, Perfluoro N-Alkyl Morpholines, 3M Fluorinert (FC-770, FC-3283, FC-40, FC-43, FC-70, FC-75, FC-77), and combinations thereof.

Generally, the amount of lubricant or organic solvent blended with the PTFE resin and the second polymer may vary. For example, in some embodiments, the lubricant or organic solvent is present in the mixture of PTFE, second polymer, and lubricant (referred to herein as the "PTFE composite material") in an amount of between about 25% to about 55%, about 30% to about 50%, or about 35% to about 45% by volume, based on the total volume of the PTFE composite. Without intending to be bound by theory, it should be noted that the lubricant/organic solvent content should remain as low as possible (while achieving the desired lubrication effect) to minimize the amount of lubricant/organic solvent that must be removed in the later devolatilization step which will be discussed herein in more detail. Likewise, it should be noted that increasing the amount of lubricant/organic solvent in the PTFE composite material can help to maintain the extruder pressure within a reasonable/maximum limit during the extrusion process. For example, use of a lubricant/organic solvent in the PTFE composite material can affect the wettability/surface tension and viscosity of the PTFE composite material and thus can be modified accordingly to provide the desired impact on the pressure during the extrusion process.

The second polymer can vary and can include one or more types of polymers. Certain non-limiting examples of suitable second polymers include, but are not limited to, polyolefins, modified polyolefins, fluoropolymers, modified fluoropolymers, polyesters, modified polyesters, polyurethanes, modified polyurethanes, polyimides, polyamides, polyamines, and various derivatives, combinations, and copolymers thereof. In some embodiments, the second polymer may comprise a modified or unmodified polyarylketone (PAEK) or a modified or unmodified polyetheretherketone (PEEK). In some embodiments, the second polymer may comprise a polyimide (PI), ultra high molecular weight polyethylene (UHMWPE), fluorinated ethylene propylene (FEP), or perfluoroalkoxy alkane (PFA).

In some embodiments, a second PTFE can be used as the second polymer, which is different in some manner than the PTFE resin component. For example, in some embodiments, the second polymer comprises sintered PTFE, PTFE that has been reground (e.g., ground following extrusion to provide it in particle, e.g., powder form), PTFE that has been chemically modified in some way, or PTFE that falls within two or more of these classifications. Examples of chemical modifications to PTFE or other polymers include, but are not limited to, grafting, oxidation, defluorination, etching, plasma treatment, and irradiation.

The second polymer is generally in the form of a plurality of polymeric particles, for example, as a finely ground powder of the plurality of polymeric particles. The second polymer (e.g., polymeric particles of the second polymer) is advantageously introduced to incorporate a desired percentage of the second polymer in the resulting preform and in the final composite tube. In such embodiments, those polymeric particles may have a particle size of less than about 150 microns, less than about 100 microns, or less than about 50 microns. In some embodiments, the polymeric particles may have a particle size in the range of about 1 to about 150 microns, about 1 to about 100 microns, or about 1 to about 50 microns. In some embodiments, the second polymer/polymeric particles may be present in an amount of less than about 50% by weight, less than about 40% by weight, less than about 30% by weight, less than about 20% by weight, or less than about 10% by weight, based on the total weight of the PTFE composite tube. In some embodiments, the second polymer/polymeric particles may be present in an amount of about 1% to about 50% by weight, about 1% to about 25% by weight, or about 1% to about 10% by weight, based on the total weight of the PTFE composite tube.

The order of mixing the various components of the PTFE composite is not intended to be limiting and the individual components of the PTFE composite material may be combined and mixed in any order as desired. For example, in certain embodiments, the second polymer may be blended with the PTFE resin either before or after addition of the lubricant or organic solvent. Subsequently, the mixture of the PTFE resin, the second polymer, and the lubricant or organic solvent may be mixed, e.g., using a low shear blending mixer or the like. It should be noted that the PTFE resin is shear sensitive and thus, it is important to take care in mixing the components of the PTFE composite material. For example, the lubricant or organic solvent is, in some embodiments, added prior to mixing to ensure uniform mixing of the PTFE composite material.

Once a PTFE composite material is provided, e.g., according to step 12 described herein, the material is subjected to compression/compounding step 14 to create a preform. The compounding or compacting of the PTFE composite material can be performed using any method known in the art and is not meant to be particularly limiting. For example, in some embodiments, the PTFE composite material can be compounded using a compactor to provide a compounded PTFE composite material suitable for extrusion at operation 16. Generally, it can be beneficial to remove at least some air from the compounded PTFE composite material prior to extrusion in order to prevent defects in the extrudate. For example, such air removal is achieved by preforming the PTFE composite material during the compounding step into various shapes (e.g., cylindrical shapes) or preforms, e.g., referred to as billets. The billets are typically loaded into the extruder shortly after production to prevent lubricant/organic solvent evaporation. In some embodiments, other additives, such as pigments, stabilizers, colorants, and/or other fillers can be added to the PTFE composite material during compounding to elicit certain properties, e.g., such as colors, radio-opacity, and the like.

After compounding the PTFE composite material, the compounded PTFE composite material is extruded, e.g., via a multi-stage extrusion process. The extrusion generally can be conducted, e.g., via paste extrusion processes. For example, the preforms or billets can be subjected to extrusion 16, e.g., by a paste extrusion machine, and later sintered 20 to form films, tubes or rods, thereby incorporating the second polymer into the product that is extruded (e.g., the film, tube, rod, etc.), creating a PTFE composite extrudate (e.g., a PTFE composite tube). Typically, during the extrusion processing, some percentage of molecular chain orientation can be imparted into the extruded product (e.g., the PTFE composite tubes) based on the drawdown of the material, e.g., much like other polymer extrusion processes. Orientation imparted into a material can impact tensile properties such as the modulus, tensile strength, and elongation. Due to the very high melt viscosity of PTFE resins, a PTFE composite tube cannot typically be produced by melt extrusion and thus, paste extrusion is a useful approach.

During the extrusion step 16, the billets can be inserted into the extrusion cylinder/barrel of a paste extruder and then pressed through a die with the help of a ram. In some embodiments, the extrusion tubes require the presence of a mandrel in the barrel and a metallic substrate (e.g., such as a wire substrate) can be fed through the mandrel. The material of the metallic substrate is not particularly limiting, for example, the metallic substrate may comprise copper (e.g., such as an annealed copper wire), plated copper (e.g., such as a silver-plated copper wire), nickel, stainless steel, nitinol, and the like. Next, the extruded paste material is formed into a tube through the extruder head.

As referenced herein, a paste extrusion process generally comprises extruding the extruded paste material through one or more dies to shape it; the resulting shaped material is then devolatilized and sintered. In some embodiments, as the extrusion pressure changes during processing, the machine design ensures that ram speed and extrusion speed are maintained at constant levels. Extruder design such as barrel size, extruder size and design, and operating conditions such as barrel zone temperatures, ram speed, and throughput can be adjusted. In some embodiments, such parameters are manipulated to influence the rate and extent of polymer degradation. One of skill in the art will recognize the considerations associated with selecting the appropriate parameters for extrusion based, e.g., on the rheology of the polymeric resin, to ensure a suitable extrudate is produced.

After the extrusion step 16, the residual lubricant/organic solvent in the extruded PTFE composite material is removed (and advantageously, completely removed) by heating the extruded PTFE composite material above the boiling point of the lubricant/organic solvent. As shown in FIG. 1, this process can be accomplished using a vaporizing or devolatilization step 18. In some embodiments, for example, the extruded PTFE composite material can be passed through a devolatilization oven to heat the extruded PTFE composite material, thereby removing any residual lubricant or organic solvent therein.

Following the vaporizing/devolatilization step, the extruded PTFE composite material can be subjected to a sintering step 20, e.g., as shown in FIG. 1. For example, the extruded PTFE composite material can be heated in a sintering oven to sinter the PTFE resin in the extruded PTFE composite material such that the PTFE resin particles adhere to each other. In some embodiments, the sintering oven can be set to a temperature equal to or higher than the melting point of PTFE (e.g., approximately 327° C.). However, it should be noted that the temperature within the sintering oven may vary as desired, e.g., based on the line speed associated with passing the extruded PTFE composite material through the oven and the thickness of the PTFE composite layer. As noted above, any amount of lubricant or organic solvent is typically removed during the vaporizing step 18 and thus, the sintering oven is generally allowed to operate free of any residual lubricant or organic solvent therein. It should be noted that the second polymer as described herein generally can withstand the sintering temperatures during this step without undue degradation. The sintered extrudate may be cooled using various methods which are known. For example, the extrudate can be passively cooled for a specified time, e.g., with air; it can be cooled via a water bath at a set temperature; or can be cooled through the action of a blower or fan.

After sintering and cooling, the PTFE composite tubes may be subjected to one or more secondary processes 22 to impart one or more additional properties and characteristics to the PTFE composite tube. In certain embodiments, the PTFE composite tubes can optionally be further processed, e.g., by cutting longer tubes into shorter lengths as desired, e.g., for specific applications or end uses. Although this step is shown in FIG. 1 as the final step of the process, it is noted that various secondary processes can be conducted at other stages of the process (e.g., a tube can be cut into shorter lengths before or after sintering). As such, the order of steps as shown in FIG. 1 is not strictly limited to the order shown therein. Example secondary processes include, but are not limited to, draw down, convoluting, spiral cutting, cuffing, etching, expanding, drilling/punching, flaring, flanging, sealing, marking, overmolding, pad printing, scoring, skiving, slitting, tapering, and tipping. Such processes can be conducted, e.g., as generally known in the art.

It should be noted that, during any step of the PTFE composite extrusion process, the extruded PTFE composite can be drawn down or reduced in size by pulling the extrudate at a faster rate than it is being extruded by the extrusion ram. In some embodiments, the degree of drawdown can be correlated with the amount of orientation that is imparted into the extrudate, for example, altering its mechanical properties to a desired specification, including, but not limited to, storage modulus, yield stress, ultimate tensile stress, and elongation. The degree and or amount of drawdown may vary as would be understood by those skilled in the art. In some embodiments, for example, the degree of drawdown of the extruded PTFE composite tube may be at least about 5 times its original length, at least about 10 times its original length, at least about 15 times its original length, at least about 20 times its original length, at least about 25 times its original length, or at least about 30 times its original length.

The PTFE composite tubes resulting from the disclosed process uniquely exhibit a lower coefficient of friction as compared to a comparable PTFE tube and a lower storage modulus as compared to a comparable PTFE tube. In particular, it is believed that extruding a PTFE tube incorporating a second polymer (e.g., in particle form), giving a PTFE composite tube in this manner, can provide a PTFE composite tube for use as a liner for catheters or other applications exhibiting particularly advantageous properties within temperature ranges, e.g., of about 20° C. to about 40° C. For example, PTFE composite tubes as described herein may advantageously exhibit one or more of the following beneficial properties when compared to a comparable PTFE tube that has not been prepared according to the methods and processes described herein:

A lower coefficient of friction as compared to a comparable PTFE tube at 23° C.

A lower change in coefficient of friction from about 23° C. to about 40° C. as compared to a comparable PTFE tube.

A coefficient of friction of about 0.07 or less at 23° C.

An increase in coefficient of friction of about 0.02 or less from about 23° C. to about 40° C.

A lower storage modulus as compared to a comparable PTFE tube at 20° C.

A reduced change in storage modulus between 20° C. to 40° C. as compared to a comparable PTFE tube.

A storage modulus of about $15 \times 10^8$ Pa or less at 20° C.

A decrease in storage modulus of about $7.5 \times 10^8$ Pa or less from about 20° C. to about 40° C.

It should be noted that the change in coefficient of friction (COF) can be determined based on Equation (1) below and the change in storage modulus can be determined based on Equation (2) below.

Equations $$\Delta COF = COF_{40° C.} - COF_{23° C.} \quad (1)$$

$$\Delta E' = \Delta E'_{40° C.} - \Delta E'_{20° C.} \quad (2)$$

These and other features of the disclosed PTFE composite tubes are beneficial, e.g., in many applications requiring improved lubricity of PTFE-based extruded polymer films, profiles and tubes, e.g., such as use in various catheter technologies and the like. As an example, in one implementation of the embodiments disclosed herein, the reduction in variation in modulus is desirable in imparting consistency to the feel of a catheter during minimally invasive procedures. Likewise, in one or more implementations of the embodiments disclosed herein, the reduction in the COF is desirable in providing increased lubricity in PTFE composite tubes which can be used in catheter technologies (e.g., serving as a liner). An effect of increased lubricity of the PTFE composite tube when used in catheter based applications is a reduced deployment force of the catheter device as it is passed through the lumen of the catheter ID, which can increase the likelihood of a successful procedure, for example. In addition to the particular benefits noted herein, it should be noted that PTFE composite tubes having reduced COF (e.g., increased lubricity) and lower variation in modulus may provide benefits when used in various other applications as would be understood by those skilled in the art.

EXAMPLES

Aspects of the present invention are more fully illustrated by the following examples, which are set forth to illustrate certain aspects of the present invention and are not to be construed as limiting thereof.

Example 1

Two sets of PTFE composite tubing were ram extruded to an outside diameter (OD) of 0.080" with a 0.002" wall thickness. The first set of PTFE composite tubing was prepared using 98 weight % PTFE and 2 weight % PEEK based on the total weight of the tube and is represented in Table 1 below as EX 1 (2% PEEK). The second set of PTFE composite tubing was prepared using 96 weight % PTFE and 4 weight % PEEK and is represented in Table 1 below as EX 1 (4% PEEK). The PEEK polymer particle size for both sets of tubing was 10 μm.

An Instron 5965 dual column mechanical tester running Bluehill 3 v3.73.4823 operating software was used to determine the tensile properties of the PTFE composite tubes. The test was performed at a rate of 20 in/min using a 1 kN (224.8 lbf) load cell attached to pneumatic grips with smooth face inserts set to a 2-inch gage length. At least 5 specimens were tested of each loading, and the average result was reported in Table 1.

The Storage Modulus (E') was obtained using a TA instruments Q800 Dynamic Mechanical Analysis ("DMA") with the film tension fixture to determine the thermomechanical properties of the PTFE composite tubes. A temperature scan was performed from −100° C. to 300° C. with an isothermal hold for five minutes at −100° C. The sample was heated at a constant rate of 3° C./min while being displaced at a constant amplitude of 15 μm with a fixed frequency tensile oscillation of 1 Hz. An additional temperature scan was performed from −20° C. to 100° C. at 3° C./min while being displaced at a constant amplitude of 15 μm with a fixed frequency tensile oscillation of 1 Hz. The resulting DMA data was imported into TA instruments TRIOS software v4.3. and the averages are listed in Table 1.

The Coefficient of Friction (COF) was obtained using a TA instruments Discovery Hybrid Rheometer (DHR-3) with the tribo-rheometer accessory to determine the tribological properties of the PTFE tubes. The samples were prepared by attaching three tubing sections of 5 mm×16.5 mm, each, to the three teeth of the half-ring for use with a Ring-On-Plate tribo-rheometry fixture. The ring with mounted samples was then attached to the ring-on-plate upper-geometry holder and lowered to have the samples contact a mirror-finish stainless steel plate at the specified axial force. A tribological test was performed at room temperature (23° C.) from sliding speeds of 750 µm/s to 7650 µm/s under an axial load of 1N. An additional tribological test was performed at 40° C. with a 5-minute dwell time at 40° C. from sliding speeds of 750 µm/s to 7650 µm/s under an axial load of 1N. Minimum COF over the stated range in sliding speed was calculated by the TA instruments TRIOS software v4.3. At least 3 samples were tested for each loading and temperature, and the averages are listed in Table 1.

Example 2

Two sets of PTFE composite tubing were ram extruded to an OD of 0.080" with a 0.002" wall thickness. The first set of PTFE composite tubing was prepared using 98 weight % PTFE and 2 weight % PFA based on the total weight of the tube and is represented in Table 1 below as EX 2 (2% PFA). The second set of PTFE composite tubing was prepared using 96 weight % PTFE and 4 weight % PFA and is represented in Table 1 below as EX 2 (4% PFA). The PFA polymer particle size was 30 µm. Testing for each of the tubes was conducted as in Example 1. The averages are reported in Table 1.

Example 3

Two sets of PTFE composite tubing were ram extruded to an OD of 0.080" with a 0.002" wall thickness. The first set of PTFE composite tubing was prepared using 98 weight % PTFE and 2 weight % FEP based on the total weight of the tube and is represented in Table 1 below as EX 3 (2% FEP). The second set of PTFE composite tubing was prepared using 96 weight % PTFE and 4 weight % FEP and is represented in Table 1 below as EX 3 (4% FEP). The FEP polymer particle size was 20 µm. Testing for each of the tubes was conducted as in Example 1, and the averages are reported in Table 1.

Example 4

Two sets of PTFE composite tubing were ram extruded to an OD of 0.080" with a 0.002" wall thickness. The first set of PTFE composite tubing was prepared using 98 weight % PTFE and 2 weight % UHMWPE based on the total weight of the tube and is represented in Table 1 below as EX 4 (2% UHMWPE). The second set of PTFE composite tubing was prepared using 96 weight % PTFE and 4 weight % UHMWPE and is represented in Table 1 below as EX 4 (4% UHMWPE). The UHMWPE polymer particle size was 10 µm. Testing for each of the tubes was conducted as in Example 1, and the averages are reported in Table 1.

Example 5

Four sets of PTFE composite tubing were ram extruded to an OD of 0.095" with a 0.002" wall thickness. The first set of PTFE composite tubing was prepared using 98 weight % PTFE and 2 weight % PTFE-A based on the total weight of the tube and is represented in Table 1 below as EX 5 (2% PTFE-A). The second set of PTFE composite tubing was prepared using 96 weight % PTFE and 4 weight % PTFE-A and is represented in Table 1 below as EX 5 (4% PTFE-A). The first set of PTFE composite tubing was prepared using 90 weight % PTFE and 10 weight % PTFE-A based on the total weight of the tube and is represented in Table 1 below as EX 5 (10% PTFE-A). The second set of PTFE composite tubing was prepared using 75 weight % PTFE and 25 weight % PTFE-A and is represented in Table 1 below as EX 5 (25% PTFE-A). The PTFE-A polymer particle size was 5 µm and was a fully sintered PTFE micropowder. Testing for each of the tubes was conducted as in Example 1, and the averages are reported in Table 1.

Example 6

Two sets of PTFE composite tubing were ram extruded to an OD of 0.095" with a 0.002" wall thickness. The first set of PTFE composite tubing was prepared using 98 weight % PTFE and 2 weight % PTFE-B based on the total weight of the tube and is represented in Table 1 below as EX 6 (2% PTFE-B). The second set of PTFE composite tubing was prepared using 96 weight % PTFE and 4 weight % PTFE-B and is represented in Table 1 below as EX 6 (4% PTFE-B). The PTFE-B polymer particle size was 38 µm and was an unsintered PTFE powder. Testing for each of the tubes was conducted as in Example 1, and the averages are reported in Table 1.

Example 7

Two sets of PTFE composite tubing were ram extruded to an OD of 0.100" with a 0.002" wall thickness. The first set of PTFE composite tubing was prepared using 98 weight % PTFE and 2 weight % PTFE-C based on the total weight of the tube and is represented in Table 1 below as EX 7 (2% PTFE-C). The second set of PTFE composite tubing was prepared using 98 weight % PTFE and 2 weight % PTFE-C and is represented in Table 1 below as EX 7 (2% PTFE-C). The PTFE-C polymer particle size was 5 µm and was a fully sintered, chemically modified PTFE micropowder. Testing for each of the tubes was conducted as in Example 1, and the averages are reported in Table 1.

Comparative Example 1

The procedure of Example 1 was used to extrude a PTFE control tube (e.g., virgin PTFE). The PTFE control tube was prepared using 100 weight % virgin PTFE based on the total weight of the tube and is represented in Table 1 below as CE 1 (Control). Testing for the tubes was conducted as in Example 1, and the averages are reported in Table 1. This comparative example is the control tube.

Comparative Example 2

Two sets of PTFE composite tubing were ram extruded to an OD of 0.080" with a 0.002" wall thickness. The first set of PTFE composite tubing was prepared using 98 weight % PTFE and 2 weight % spherical glass based on the total weight of the tube and is represented in Table 1 below as CE 2 (2% glass). The second set of PTFE composite tubing was prepared using 96 weight % PTFE and 4 weight % PEEK and is represented in Table 1 below as CE 2 (4% glass). The glass filler particle size was 10 µm.

Testing for each of the tubes was conducted as in Example 1, and the averages are reported in Table 1. This comparative example provides insight into how an inorganic filler under the same processing conditions of comparable particle sizes may not elicit a similar response for COF and moduli parameters to an organic filler/polymeric particle.

Comparative Example 3

PTFE composite tubing were ram extruded to an OD of 0.060" with a 0.002" wall thickness. The PTFE composite tubing was prepared using 98 weight % PTFE and 4 weight % PEEK based on the total weight of the tube and is represented in Table 1 below as CE 3 (4% PEEK-LDD). The PEEK polymer particle size was 10 μm. This extrusion deviated from Example 1 in that this extrusion's process parameters exhibited significantly less drawdown (approximately 23% reduction in drawdown) causing the PTFE tubing to have a reduced machine-direction/axial orientation.

Testing for each of the tubes was conducted as in Example 1, and the averages are reported in Table 1 as "4% PEEK-LDD". This comparative example provides insight into how processing the same PTFE/PEEK formulation differently will elicit a different response for COF and moduli parameters.

Figure 4:
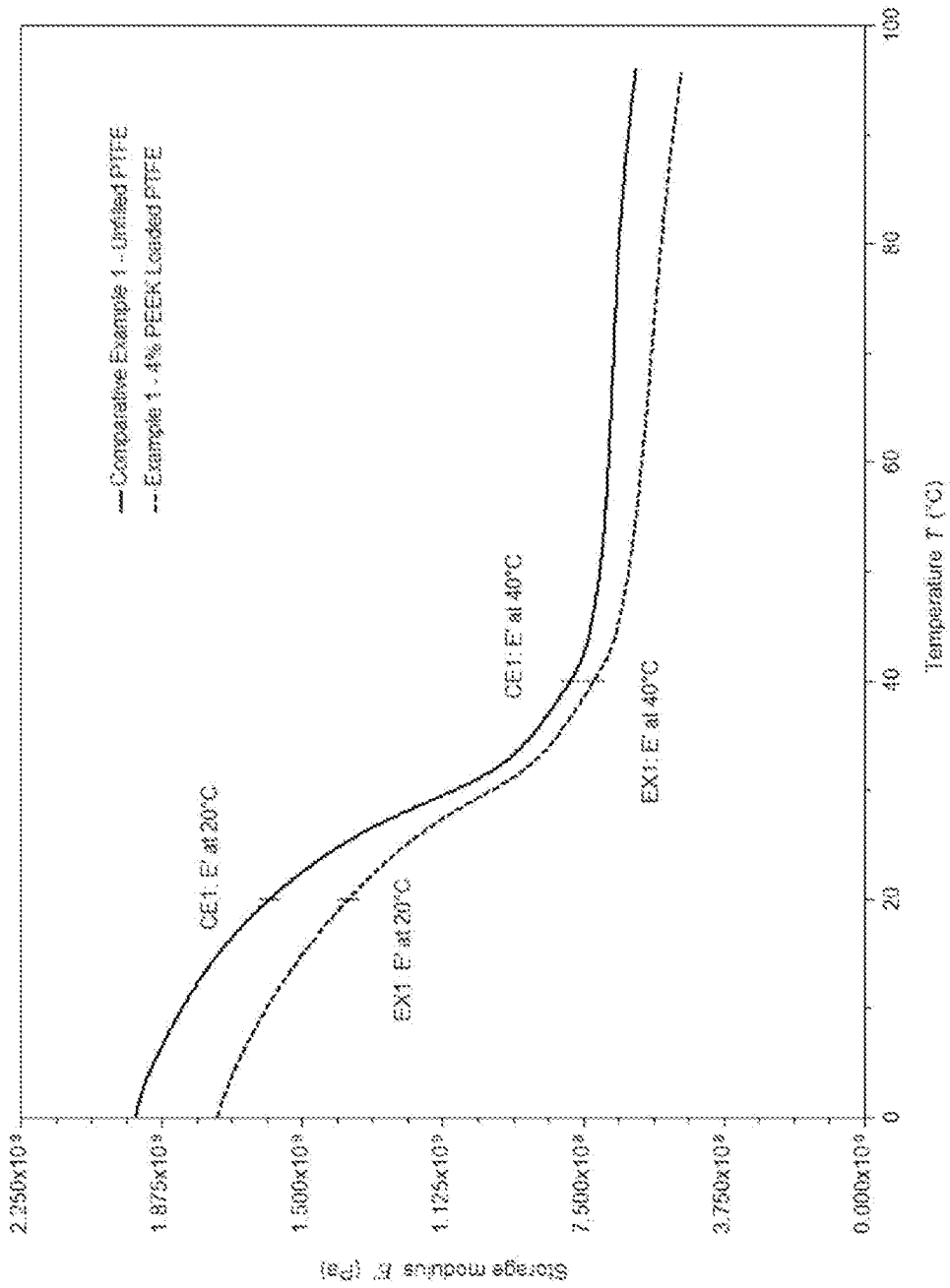
FIG. 4 is a plot of storage modulus versus temperature for a PTFE composite tube compared to a PTFE tube according to certain embodiments of the present disclosure.

FIG. 4 depicts a plot of storage modulus (E') versus temperature for the PTFE composite tube prepared according to Example 1 above (e.g., including 96% PTFE and 4% PEEK by weight) as compared to the control tube prepared according to Comparative Example 1 above (e.g., including 100% virgin PTFE by weight). As shown in FIG. 4, the PTFE composite tube prepared according to Example 1 demonstrated significantly lower storage modulus as compared to the control tube irrespective of the temperature.

Many modifications and other embodiments of the invention will come to mind to one skilled in the art to which this invention pertains having the benefit of the teachings presented in the foregoing description. Therefore, it is to be understood that the invention is not to be limited to the specific embodiments disclosed and that modifications and other embodiments are intended to be included within the scope of the appended claims. Although specific terms are employed herein, they are used in a generic and descriptive sense only and not for purposes of limitation.

What is claimed is:

1. A PTFE composite tube comprising PTFE and a second polymer,

TABLE 1

Summary of Test Results

| | | COF | | | DMA, $\times 10^8$ Pa | | | Tensile | | |
|---|---|---|---|---|---|---|---|---|---|---|
| | | 23° C. | 40° C. | $-\Delta$COF | E' (20° C.) | $-\Delta$E' | % | Modulus, $\times 10^8$ Pa | UTS, $\times 10^8$ Pa | Elongation (%) |
| EX1 | 2% PEEK | 0.060 | 0.065 | −0.005 | 19.54 | 9.57 | 48.98 | 19.09 | 0.72 | 92 |
| EX1 | 4% PEEK | 0.059 | 0.058 | 0.001 | 13.78 | 6.56 | 47.61 | 17.97 | 0.68 | 64 |
| EX2 | 2% PFA | 0.059 | 0.053 | 0.006 | 10.00 | 4.59 | 45.90 | 13.26 | 0.53 | 18 |
| EX2 | 4% PFA | 0.057 | 0.059 | −0.002 | 10.33 | 4.88 | 47.24 | 13.19 | 0.51 | 11 |
| EX3 | 2% FEP | 0.065 | 0.056 | 0.009 | 11.61 | 5.30 | 45.65 | 15.12 | 0.63 | 13 |
| EX3 | 4% FEP | 0.060 | 0.064 | −0.004 | 11.70 | 5.28 | 45.13 | 14.72 | 0.60 | 19 |
| EX4 | 2% UHMWPE | 0.055 | 0.067 | −0.012 | 12.71 | 6.03 | 47.44 | 14.60 | 0.67 | 88 |
| EX4 | 4% UHMWPE | 0.056 | 0.058 | −0.002 | 15.97 | 7.81 | 48.90 | 14.54 | 0.65 | 55 |
| EX5 | 2% PTFE-A | 0.074 | 0.061 | 0.013 | 11.95 | 5.53 | 46.28 | 12.20 | 0.86 | 280 |
| EX5 | 4% PTFE-A | 0.063 | 0.064 | −0.001 | 12.02 | 5.70 | 47.42 | 10.60 | 0.78 | 280 |
| EX5 | 10% PTFE-A | 0.050 | 0.054 | −0.004 | 11.13 | 4.78 | 42.95 | 12.40 | 0.77 | 278 |
| EX5 | 25% PTFE-A | 0.048 | 0.065 | −0.017 | 13.59 | 5.97 | 43.93 | 10.07 | 0.62 | 258 |
| EX6 | 2% PTFE-B | 0.052 | 0.055 | −0.003 | 13.31 | 6.78 | 50.94 | 12.32 | 0.67 | 187 |
| EX6 | 4% PTFE-B | 0.048 | 0.048 | 0.000 | 13.30 | 6.52 | 49.02 | 10.99 | 0.59 | 171 |
| EX7 | 2% PTFE-C | 0.049 | 0.054 | −0.004 | 8.67 | 3.77 | 43.48 | 10.98 | 0.77 | 281 |
| CE1 | Control | 0.076 | 0.100 | −0.024 | 15.88 | 8.03 | 50.57 | 19.08 | 1.08 | 256 |
| CE2 | 2% Glass | 0.073 | 0.083 | −0.010 | 11.91 | 5.50 | 46.18 | 14.85 | 1.00 | 219 |
| CE2 | 4% Glass | 0.071 | 0.085 | −0.014 | 13.18 | 6.13 | 46.51 | 14.97 | 0.89 | 185 |
| CE3 | 4% PEEK-LDD | 0.074 | 0.091 | −0.017 | 10.42 | 4.30 | 41.27 | 8.53 | 0.74 | 252 |

SUMMARY OF FIGURES

Figure 2:
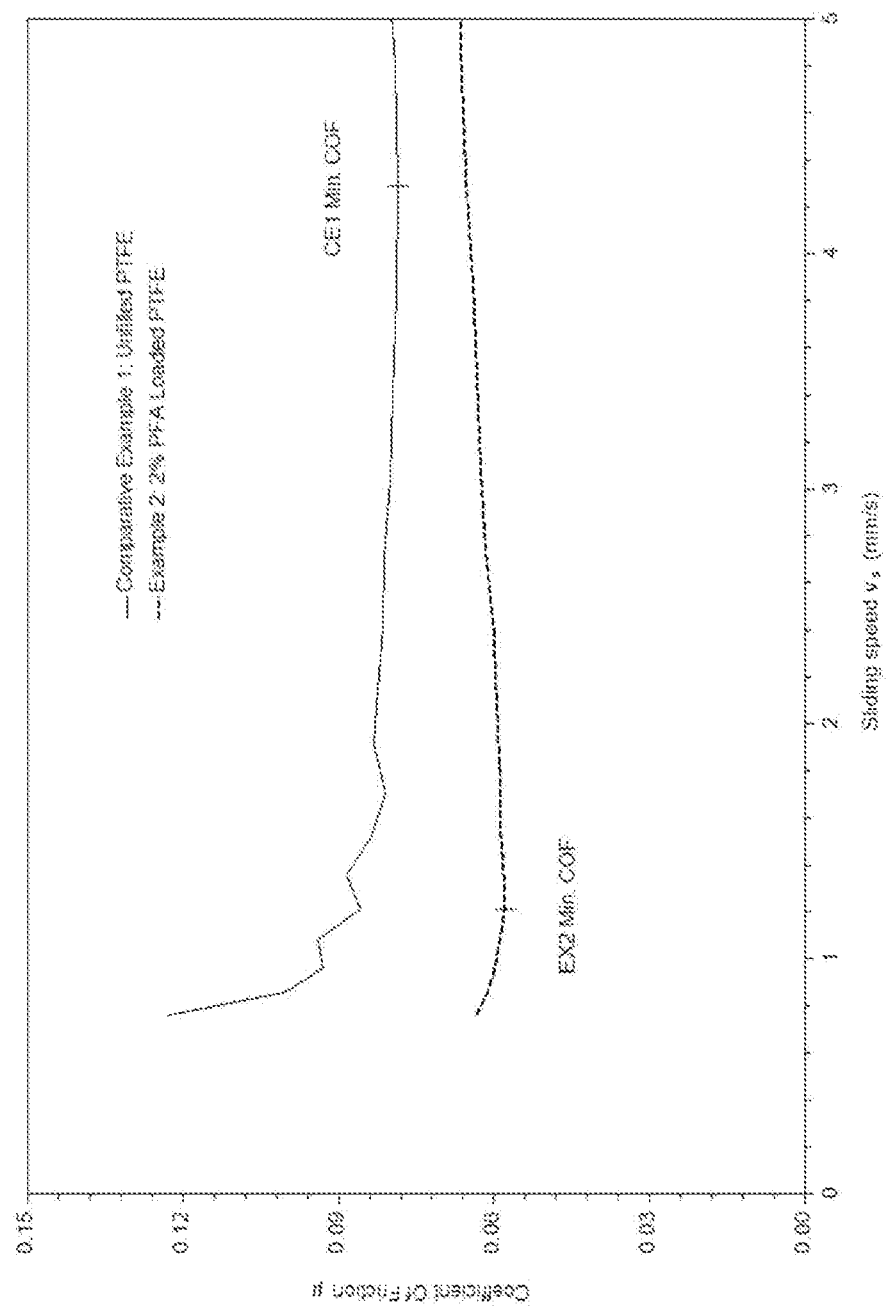
FIG. 2 is a plot of COF versus sliding speed for a PTFE composite tube compared to a PTFE tube according to certain embodiments of the present disclosure.

FIG. 2 depicts a plot of COF versus sliding speed for the PTFE composite tube prepared according to Example 2 above (e.g., including 98% PTFE and 2% PFA by weight) compared to the control tube prepared according to Comparative Example 1 above (e.g., including 100% virgin PTFE by weight). As shown in FIG. 2, the PTFE composite tube prepared according to Example 2 demonstrated a significantly lower COF as compared to the control tube irrespective of the sliding speed.

Figure 3:
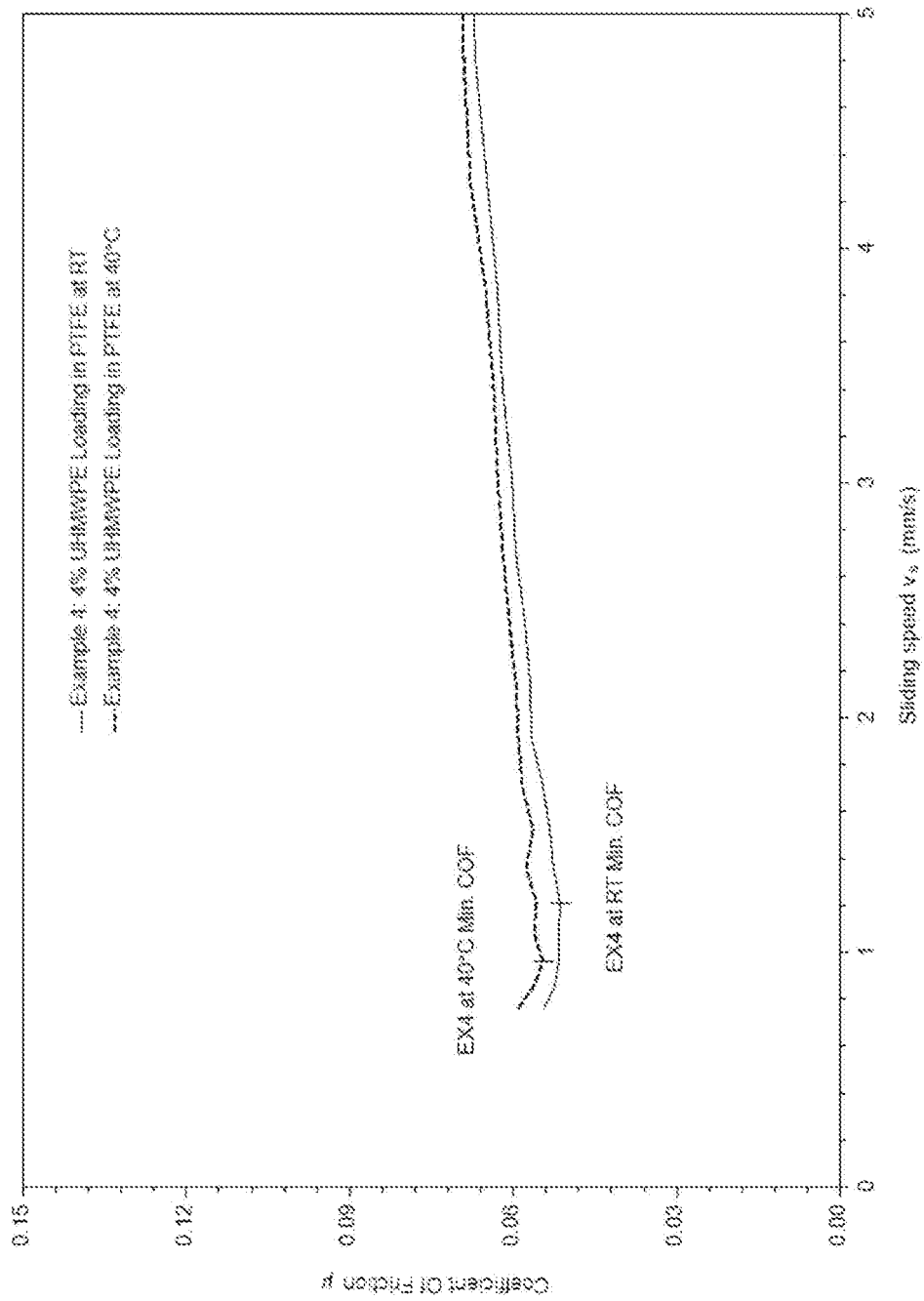
FIG. 3 is a plot of COF versus sliding speed for a PTFE composite tube at 23° C. and 40° C. according to certain embodiments of the present disclosure.

FIG. 3 depicts a plot of COF versus sliding speed for the PTFE composite tube prepared according to Example 4 above (e.g., including 96% PTFE and 4% UHMWPE by weight) at 23° C. and 40° C., respectively. As shown in FIG. 3, the observed COF of both samples was not significantly affected by the change in temperature as the COF of the sample remained substantially the same at both temperatures and irrespective of the sliding speed.

wherein the second polymer is present in a concentration of less than about 10% by weight of the PTFE composite tube, wherein the PTFE composite tube exhibits one or both of:
    a lower coefficient of friction as compared to a comparable PTFE tube when tested at 23° C.; and
    a smaller change in coefficient of friction from about 23° C. to about 40° C. as compared to a comparable PTFE tube, the comparable PTFE tube not comprising the second polymer, wherein the PTFE composite tube has a wall thickness of less than about 0.1 mm, and wherein the PTFE composite tube is in sintered form.

2. The PTFE composite tube of claim 1, wherein the PTFE composite tube exhibits a coefficient of friction of about 0.07 or less at 23° C. and an increase in coefficient of friction of about 0.02 or less from about 23° C. to about 40° C.

3. The PTFE composite tube of claim 1, wherein the PTFE composite tube exhibits a lower storage modulus as compared to the comparable PTFE tube at 20° C. and a reduced change in storage modulus between 20° C. to 40° C. as compared to the comparable PTFE tube.

4. The PTFE composite tube of claim 1, wherein the PTFE composite tube exhibits a storage modulus of about $15 \times 10^8$ Pa or less at 20° C. and a decrease in storage modulus of about $7.5 \times 10^8$ Pa or less from about 20° C. to about 40° C.

5. The PTFE composite tube of claim 1, wherein the second polymer is a polyolefin or modified polyolefin.

6. The PTFE composite tube of claim 1, wherein the second polymer is a fluoropolymer or a modified fluoropolymer.

7. The PTFE composite tube of claim 1, wherein the second polymer is a polyarylketone (PAEK), a polyetheretherketone (PEEK), or a modified PAEK or PEEK.

8. The PTFE composite tube of claim 1, wherein the second polymer is a polyester or modified polyester.

9. The PTFE composite tube of claim 1, wherein the second polymer is a polyurethane or modified polyurethane.

10. The PTFE composite tube of claim 1, wherein the second polymer is a polyimide, polyamide, polyamine, or a copolymer thereof.

11. The PTFE composite tube of claim 1, wherein the second polymer is in the form of a plurality of polymeric particles having an average particle size of less than about 100 microns.

12. The PTFE composite tube of claim 1, wherein the second polymer is a second, different PTFE selected from the group consisting of sintered PTFE, reground PTFE, PTFE of a different grade, chemically modified PTFE, and combinations thereof.

13. The PTFE composite tube of claim 1, wherein the second polymer is selected from the group consisting of polyaryletherketone (PAEK), modified polyaryletherketone (modified PAEK), polyetheretherketone (PEEK), modified polyetheretherketone (modified PEEK), polyimide (PI), ultra high molecular weight polyethylene (UHMWPE), fluorinated ethylene propylene (FEP), perfluoroalkoxy alkane (PFA), and combinations or copolymers of any two or more thereof.

14. The PTFE composite tube of claim 1, wherein the comparable PTFE tube is an unfilled PTFE tube.

15. The PTFE composite tube of claim 1, wherein the comparable PTFE tube is a virgin PTFE tube.

16. A medical device comprising the PTFE composite tube of claim 1.

17. The medical device of claim 16, wherein the medical device is a catheter.

18. The PTFE composite tube of claim 1, wherein the PTFE is homopolymeric PTFE.

19. The PTFE composite tube of claim 1, prepared via a paste extrusion process.

20. A PTFE composite tube comprising PTFE and a second polymer,
    wherein the second polymer is present in a concentration of less than about 10% by weight of the PTFE composite tube,
    wherein the PTFE composite tube exhibits one or both of:
        a lower storage modulus as compared to a comparable PTFE tube at 20° C.; and
        a smaller change in storage modulus between 20° C. to 40° C. as compared to a comparable PTFE tube, the comparable PTFE tube not comprising the second polymer,
    wherein the PTFE composite tube has a wall thickness of less than about 0.1 mm, and
    wherein the PTFE composite tube is in sintered form.

21. The PTFE composite tube of claim 20, wherein the PTFE composite tube exhibits a storage modulus of about $15 \times 10^8$ Pa or less at 20° C. and a decrease in storage modulus of about $7.5 \times 10^8$ Pa or less from about 20° C. to about 40° C.

22. A medical device comprising:
    a PTFE composite tube, the PTFE composite tube comprising:
        PTFE and a second polymer, the second polymer concentration being less than about 10% by weight of the PTFE composite tube, the PTFE composite tube exhibiting one or both of:
            a lower storage modulus as compared to a PTFE tube at 20° C.; and
            a reduced change in storage modulus between 20° C. to 40° C. as compared to a comparable PTFE tube, the comparable PTFE tube not comprising the second polymer,
        wherein the PTFE composite tube is in sintered form.

23. The medical device of claim 22, wherein the PTFE composite tube has a wall thickness of less than about 0.1 mm.

* * * * *